US009903790B2

(12) United States Patent
Schlegel et al.

(10) Patent No.: US 9,903,790 B2
(45) Date of Patent: Feb. 27, 2018

(54) METHOD AND DEVICE FOR THE OPERATION OF A BINARY LAMBDA SENSOR ARRANGED IN AN EXHAUST GAS TRACT OF AN INTERNAL COMBUSTION ENGINE

(71) Applicant: Continental Automotive GmbH, Hannover (DE)

(72) Inventors: Sirko Schlegel, Neutraubling (DE); Jens Paggel, Abensberg (DE)

(73) Assignee: CONTINENTAL AUTOMOTIVE GMBH, Hanover (DE)

( * ) Notice: Subject to any disclaimer, the term of this patent is extended or adjusted under 35 U.S.C. 154(b) by 336 days.

(21) Appl. No.: 14/360,764

(22) PCT Filed: Nov. 27, 2012

(86) PCT No.: PCT/EP2012/073751
§ 371 (c)(1),
(2) Date: May 27, 2014

(87) PCT Pub. No.: WO2013/079489
PCT Pub. Date: Jun. 6, 2013

(65) Prior Publication Data
US 2015/0346056 A1 Dec. 3, 2015

(30) Foreign Application Priority Data
Nov. 29, 2011 (DE) .................. 10 2011 087 291

(51) Int. Cl.
*G01M 15/10* (2006.01)
*G01N 27/407* (2006.01)
(Continued)

(52) U.S. Cl.
CPC ......... *G01M 15/104* (2013.01); *F02D 41/123* (2013.01); *G01N 27/407* (2013.01);
(Continued)

(58) Field of Classification Search
CPC .. G01N 27/404–27/407; G01N 27/409; G01N 27/419; G01N 27/41; G01M 15/10;
(Continued)

(56) References Cited

U.S. PATENT DOCUMENTS

| 5,494,557 A | 2/1996 | Hotzel et al. .................. 205/784 |
| 6,676,818 B1 | 1/2004 | Schneider et al. ............. 204/424 |
| 2007/0227889 A1 | 10/2007 | Schaak et al. ................. 204/424 |

FOREIGN PATENT DOCUMENTS

| CN | 102003295 A | 4/2011 | ............. F02D 41/14 |
| DE | 4333231 A1 | 4/1995 | ........... G01N 27/406 |

(Continued)

OTHER PUBLICATIONS

International Search Report and Written Opinion, Application No. PCT/EP2012/073751, 16 pages, dated Mar. 22, 2013.
(Continued)

*Primary Examiner* — Gurpreet Kaur
(74) *Attorney, Agent, or Firm* — Slayden Grubert Beard PLLC

(57) ABSTRACT

A binary lambda sensor has a first electrode arranged on the exhaust gas side, a second electrode arranged contiguous to a reference air volume, and a power source arranged between the first and second electrode. A potential difference between the first and second electrodes forms a measurement signal of the sensor. In a measurement operation of the sensor, the power source is operated in a measurement operating state and provides the measurement signal. To adjust a specified oxygen concentration in the reference air volume, the power source is operated in a regeneration operating state. If a specified condition is fulfilled and the engine is operating in a coasting mode, the power source is operated in the measurement operating state, and a power source adjustment signal is determined for the regeneration (Continued)

operating state based on the measurement signal, for the adjustment of the specified oxygen concentration in the reference air volume.

4 Claims, 1 Drawing Sheet

(51) Int. Cl.
    *F02D 41/12*     (2006.01)
    *G01N 27/406*     (2006.01)
    *G01N 27/417*     (2006.01)
    *F02D 41/14*     (2006.01)

(52) U.S. Cl.
    CPC ..... *G01N 27/4065* (2013.01); *G01N 27/4175* (2013.01); *F02D 41/1454* (2013.01)

(58) Field of Classification Search
    CPC . G01M 15/102; G01M 15/104; F02D 41/123; F02D 41/1454
    See application file for complete search history.

(56) References Cited

FOREIGN PATENT DOCUMENTS

| | | | |
|---|---|---|---|
| DE | 19834276 A1 | 2/2000 | ........... G01N 27/407 |
| DE | 102006014697 A1 | 10/2007 | ........... G01N 27/407 |
| DE | 102006060633 A1 | 6/2008 | ........... G01N 27/407 |
| DE | 102007054391 A1 | 5/2009 | ........... G01N 27/409 |
| DE | 102009027133 A1 | 12/2010 | ........... G01N 27/419 |
| DE | 102010027984 A1 | 10/2011 | .............. F01N 11/00 |
| EP | 0646789 A1 | 4/1995 | ........... G01N 27/406 |
| WO | 2010/108732 A1 | 9/2010 | ........... G01N 27/406 |
| WO | 2013/079489 A1 | 6/2013 | ............. F02D 41/12 |

OTHER PUBLICATIONS

Chinese Office Action, Application No. 201280059012.0, 11 pages, dated Jan. 6, 2016.

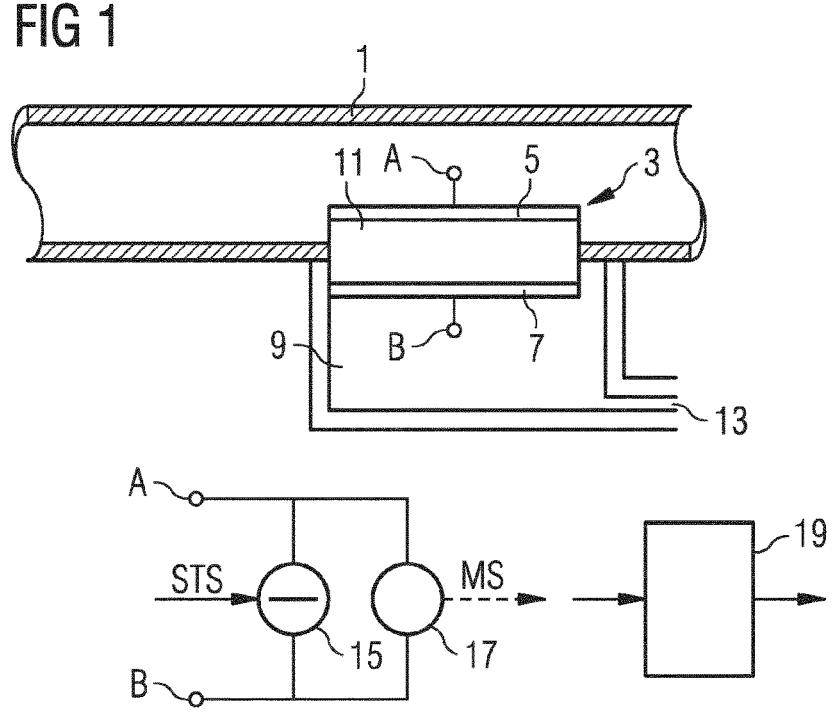
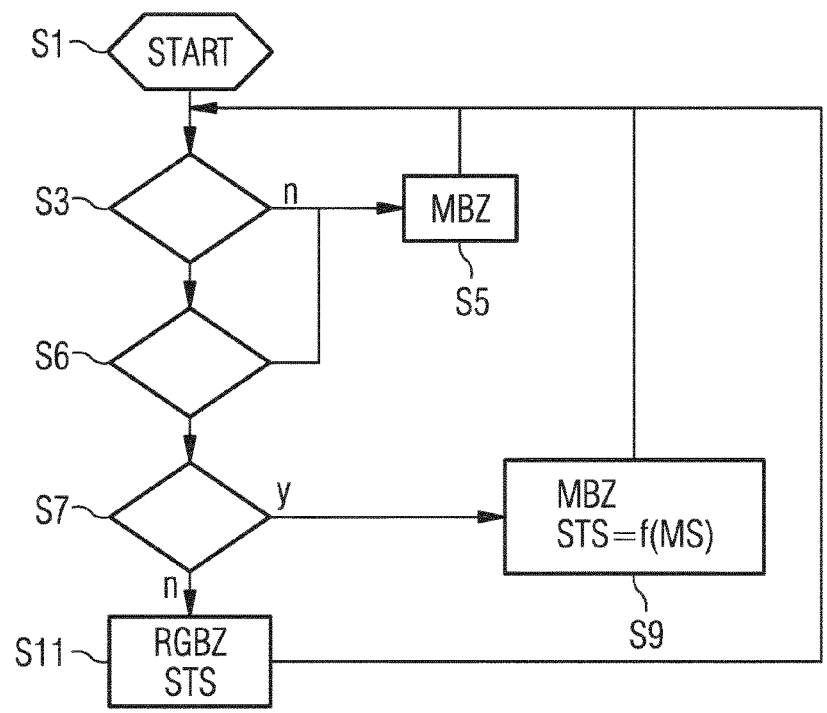

US 9,903,790 B2

METHOD AND DEVICE FOR THE OPERATION OF A BINARY LAMBDA SENSOR ARRANGED IN AN EXHAUST GAS TRACT OF AN INTERNAL COMBUSTION ENGINE

CROSS-REFERENCE TO RELATED APPLICATIONS

This application is a U.S. National Stage Application of International Application No. PCT/EP2012/073751 filed Nov. 27, 2012, which designates the United States of America, and claims priority to DE Application No. 10 2011 087 291.4 filed Nov. 29, 2011, the contents of which are hereby incorporated by reference in their entirety.

TECHNICAL FIELD

The invention relates to a method and to a device for operating a binary lambda probe which is arranged in an exhaust gas section of an internal combustion engine.

BACKGROUND

Ever stricter statutory requirements in terms of admissible emissions of pollutants by motor vehicles in which internal combustion engines are arranged make it necessary to keep the emissions of pollutants as low as possible during operation of the internal combustion engine. This can occur, on the one hand, by virtue of the fact that there is a reduction in the emissions of pollutants which are produced during the combustion of the air/fuel mixture in the respective cylinder of the internal combustion engine. On the other hand, exhaust gas post-treatment systems are in use in internal combustion engines, which exhaust gas post-treatment systems convert the emissions of pollutants which are generated during the combustion process of the air/fuel mixture in the respective cylinders into harmless substances. For this purpose, exhaust gas catalytic converters are used which convert carbon monoxide, hydrocarbons and nitrogen oxides into harmless substances. Both the targeted influencing of the generation of the emissions of pollutants during the combustion and the conversion of the components of the pollutants with a high degree of efficiency by the exhaust gas catalytic converter require a very precisely set air/fuel ratio in the respective cylinder.

In this connection, binary lambda probes are used by way of example. The measurement signal of the binary lambda probe has a magnitude of high gradient, when exhaust gas which results from a mixture of air and fuel before the combustion flows past it, when the mixture varies in a very narrow range around a stoichiometric mixture. In the case of exhaust gas which results from a mixture of air and fuel before the combustion and lies outside the narrow window around the stoichiometric mixture, the measurement signal has a very flat profile.

DE 10 2006 014 697 A1 discloses a lambda probe for motor vehicles comprising at least one reference electrode, which is arranged in a solid electrolyte, and an exhaust gas electrode, which is exposed to the exhaust gas and is provided with a porous ceramic coating. Also provided is a circuit arrangement by means of which an oxygen stream which flows to the exhaust gas electrode can be generated between the reference electrode and the exhaust gas electrode, the size of said oxygen stream being matched to the gas streams which diffuse through the porous coating such that a targeted lambda step change shift takes place.

SUMMARY

One embodiment provides a method for operating a binary lambda probe, which is arranged in an exhaust gas section of an internal combustion engine, having a first electrode, which is arranged on the exhaust gas side, and a second electrode, which is arranged so as to adjoin a reference air volume, and having a current source which is arranged electrically between the first and the second electrode, wherein a potential difference between the first and the second electrode forms a measurement signal of the binary lambda probe, in which method: during measurement operation of the binary lambda probe, the current source is operated in a measurement operation state and the measurement signal is provided; in order to set a prespecified oxygen concentration in the reference air volume, the current source is operated in a regeneration operation state, specifically for the purpose of setting the prespecified oxygen concentration in the reference air volume; and when a prespecified condition is met and the internal combustion engine is in an overrun operation state in which a supply of fuel is suppressed, the current source is operated in the measurement operation state and, depending on the measurement signal of the binary lambda probe, an actuating signal for the current source for the regeneration operation state of said current source is determined in order to set the prespecified oxygen concentration in the reference air volume.

Another embodiment provides a method for operating a binary lambda probe, which is arranged in an exhaust gas section of an internal combustion engine, having a first electrode, which is arranged on the exhaust gas side, and a second electrode, which is arranged so as to adjoin a reference air volume, and having a current source which is arranged electrically between the first and the second electrode, wherein a potential difference between the first and the second electrode forms a measurement signal of the binary lambda probe, in which method: during measurement operation of the binary lambda probe, the voltage source is operated in a measurement operation state and the measurement signal is provided; in order to set a prespecified oxygen concentration in the reference air volume, the voltage source is operated in a regeneration operation state, specifically for the purpose of setting the prespecified oxygen concentration in the reference air volume; and when a prespecified condition is met and the internal combustion engine is in an overrun operation state in which a supply of fuel is suppressed, the voltage source is operated in the measurement operation state and, depending on the measurement signal of the binary lambda probe, an actuating signal for the voltage source for the regeneration operation state of said voltage source is determined in order to set the prespecified oxygen concentration in the reference air volume.

Another embodiment provides a device for operating a binary lambda probe, which is arranged in an exhaust gas section of an internal combustion engine, having a first electrode, which is arranged on the exhaust gas side, and a second electrode, which is arranged so as to adjoin a reference air volume, and having a current source which is arranged electrically between the first and the second electrode, wherein a potential difference between the first and the second electrode forms a measurement signal of the binary lambda probe, wherein the device is designed: during measurement operation of the binary lambda probe, to operate the current source in a measurement operation state and to provide the measurement signal; in order to set a prespecified oxygen concentration in the reference air volume, to operate the current source in a regeneration operation state, specifically for the purpose of setting the prespecified oxygen concentration in the reference air volume; and when a prespecified condition is met and the internal combustion engine is in an overrun operation state in which a supply of fuel is suppressed, to operate the current source in the measurement operation state and, depending on the measurement signal of the binary lambda probe, to determine an actuating signal for the current source for the regeneration operation state of said current source in order to set the prespecified oxygen concentration in the reference air volume.

Another embodiment provides a device for operating a binary lambda probe, which is arranged in an exhaust gas section of an internal combustion engine, having a first electrode, which is arranged on the exhaust gas side, and a second electrode, which is arranged so as to adjoin a reference air volume, and having a voltage source which is arranged electrically between the first and the second electrode, wherein a potential difference between the first and the second electrode forms a measurement signal of the binary lambda probe, wherein the device is designed: during measurement operation of the binary lambda probe, to operate the voltage source in a measurement operation state and to provide the measurement signal; in order to set a prespecified oxygen concentration in the reference air volume, to operate the voltage source in a regeneration operation state, specifically for the purpose of setting the prespecified oxygen concentration in the reference air volume; and when a prespecified condition is met and the internal combustion engine is in an overrun operation state in which a supply of fuel is suppressed, to operate the voltage source in the measurement operation state and, depending on the measurement signal of the binary lambda probe, to determine an actuating signal for the voltage source for the regeneration operation state of said voltage source in order to set the prespecified oxygen concentration in the reference air volume.

BRIEF DESCRIPTION OF THE DRAWINGS

Example embodiments of the invention are explained in greater detail below with reference to the schematic drawings, in which:

FIG. 1 shows an exhaust gas section of an internal combustion engine having a binary lambda probe, and FIG. 2 shows a flowchart of a program for operating the exhaust gas probe.

DETAILED DESCRIPTION

Embodiments of the invention provide a method and a device for reliable and low-emission operation of an internal combustion engine.

According to a first aspect, the invention is directed to a method and a corresponding device for operating a binary lambda probe which is arranged in an exhaust gas section of an internal combustion engine. The binary lambda probe has a first electrode, which is arranged on the exhaust gas side, and a second electrode, which is arranged so as to adjoin a reference air volume. Said binary lambda probe further has an associated current source which is arranged electrically between the first and the second electrode. A potential difference between the first and the second electrode forms a measurement signal of the binary lambda probe. During measurement operation of the binary lambda probe, the current source is operated in a measurement operation state and the measurement signal is provided. The measurement signal can be used, for example, as part of a lambda control process.

In order to set a prespecified oxygen concentration in the reference air volume during regeneration operation of the binary lambda probe, the current source is operated in a regeneration operation state, specifically for the purpose of setting the prespecified oxygen concentration in the reference air volume. By operation of the current source in the regeneration operation state, oxygen ions are therefore transported from the exhaust gas section to the reference air volume or vice versa, and therefore the oxygen concentration in the reference air volume is correspondingly influenced.

When a prespecified condition is met and the internal combustion engine is in an overrun operation state in which a supply of fuel is suppressed, the current source is operated in the measurement operation state and, depending on the measurement signal of the binary lambda probe, an actuating signal for the current source for the regeneration operation state of said current source is determined in order to set the prespecified oxygen concentration in the reference air volume. In this way, it is simply possible to use the knowledge that, when the internal combustion engine is in the overrun operation state, the oxygen concentration in the exhaust gas section corresponds approximately to the oxygen concentration of air, specifically without the influence of the exhaust gases. In this way, a reference is simply provided for the prespecified oxygen concentration in the reference air volume and, depending on the measurement signal of the binary lambda probe, the actuating signal for the current source for the regeneration operation state of said current source can thereby be simply determined with the aim of setting the prespecified oxygen concentration in the reference air volume. The actuating signal can comprise, for example, the current direction of the current which is applied by the current source and/or the duration of the current, which is to be applied, through the current source to establish the corresponding oxygen ion transportation.

The prespecified condition can be met, for example, after a prespecified time period has elapsed. Said condition can be met, in principle, independently of an actual presence of the regeneration operation of the internal combustion engine of the binary lambda probe. If said condition is also met during regeneration operation and then the overrun operation state is also present, the regeneration operation state is terminated and the current source is operated in the measurement operation state and then operated again in the regeneration operation state, wherein this can then accordingly be performed several times in an alternating manner.

By virtue of this procedure, it is possible to counteract so-called probe contamination in a simple manner, it being possible for said probe contamination to occur, for example, in the event of relatively long-term rich operation of the binary lambda probe. Furthermore, the reference volume, which generally communicates with the ambient air, for example by means of a corresponding feed line, can also be contaminated by impurities which enter in this way, for example by carbon monoxide or carbon dioxide.

In this way, a contribution can be made to reliable operation of the binary lambda probe and therefore a contribution can be made that, in the measurement operation state, the measurement signal very precisely represents the air/fuel ratio of the mixture before the combustion, the exhaust gas which flows past the binary lambda probe resulting from said mixture.

The current source is, in particular, a switchable current source and, in particular, it may also be a current source which can be controlled.

According to a second aspect, the invention is directed to a method and a corresponding device for operating a binary lambda probe. The second aspect is distinguished from the first aspect in that a voltage source is provided instead of the current source.

An internal combustion engine has a plurality of cylinders, each of which has at least one associated gas inlet valve by means of which a supply of air can be set. Furthermore, the respective cylinder has an associated respective injection valve by means of which fuel can be supplied to a combustion chamber of the respective cylinder. Furthermore, the internal combustion engine has an exhaust gas section 1 (FIG. 1) by means of which exhaust gases can be discharged from the respective combustion chambers of the cylinders. In this connection, the internal combustion engine has respective gas outlet valves via which discharge of the exhaust gas from the combustion chambers into the exhaust gas section 1 can be controlled.

A binary lambda probe 3 is arranged in the exhaust gas section 1. The binary lambda probe 3 has a first electrode 5, which is arranged on the exhaust gas side, and a second electrode 7, which is arranged so as to adjoin a reference air volume 9. A solid-body electrolyte 11, which comprises zirconium dioxide for example, is located between the first electrode 5 and the second electrode 7. At relatively high temperatures of the solid-body electrolyte, which lie at approximately 650° for example, oxygen ions can diffuse through the solid-body electrolyte 11, specifically depending on the respective oxygen particle pressures of the exhaust gas flowing in the exhaust gas section 1 and of the gas which is located in the reference air volume 9.

The reference air volume 9 communicates with an area surrounding the internal combustion engine, preferably by means of a feed line 13 which can comprise, for example, a hose and/or can also be integrated in a cable supply means of the binary lambda probe 3. The supply line 13 is designed such that air can enter the reference air volume 9 by means of said supply line, said air being as free as possible of impurities of exhaust gas or hydrocarbons caused by fuel or oil in the region of the internal combustion engine and also exhaust gases caused by the combustion process in the internal combustion engine.

However, impurities of this kind can nevertheless undesirably enter the reference air volume, for example due to leaks in the feed line or else in the event of very long-term rich operation of the internal combustion engine. This can lead, in principle, to so-called probe contamination, in the case of which the oxygen concentration in the reference air volume 9 deviates, in particular considerably, from a prespecified oxygen concentration. The prespecified oxygen concentration is, in particular, the natural oxygen concentration in the air which surrounds the internal combustion engine and therefore that air which is also drawn in by the internal combustion engine for the combustion process.

The binary lambda probe 3 further has an associated current source 15 which is arranged electrically between the first and the second electrode 5, 7. The current source 15 can be switched and preferably also controlled. The respective operation of said current source is controlled by means of an actuating signal STS.

Furthermore, a measurement signal transmitter 17 is arranged electrically between the first and the second electrode 5, 7, said measurement signal transmitter tapping off a potential difference between the first and the second electrode 5, 7 and, depending on said potential difference, generating a measurement signal of the binary lambda probe 3.

Furthermore, a control device 19 is provided, the input end of said control device being supplied with the measurement signal MS of the binary lambda probe 3, but, in principle, further measurement signals of other sensors which are associated with the internal combustion engine also being supplied. The control device 19 is designed to generate, independently of the measurement signal or signals which are supplied to it, actuating signals for actuating devices of the internal combustion engine which may be, for example, an injection valve, a throttle flap, an exhaust gas return valve or the like. Furthermore, the control device 19 is also designed to generate the actuating signal STS for the current source 15.

The control device 19 has a data and program memory in which one or more programs for operating the internal combustion engine are stored, it being possible for said programs to then be run during operation of the internal combustion engine. To this end, the control device 19 also has a computer unit which comprises, amongst other things, a microprocessor and/or a controller. Furthermore, the control device 19 also has one or more output stages.

In order to operate the binary lambda probe 3, a program is stored in the data and program memory of the control device 19, said program being explained in greater detail below with reference to FIG. 2.

The program is started in step S1, for example soon after the internal combustion engine is started. In step S1, it is possible, for example, to initialize various variables.

In step S3, a check is made to determine whether the internal combustion engine is in a suitable operation state in which the measurement signal MS of the binary lambda probes 3 is not absolutely required for other functions, for example lambda control. If the internal combustion engine is not in a suitable operation state or one of the suitable operating states during execution of step S3, the process is continued with step S5.

In step S5, a measurement operation of the binary lambda probe 3 is assumed, in which the current source 15 is operated in a measurement operation state MBZ and the measurement signal MS is provided. Said measurement signal is then used, for example, for carrying out lambda control.

In the measurement operation state MBZ, the current source 15 is, in particular, deactivated, this being controlled by an actuating signal STS of corresponding design. However, in principle, said current source can also be activated in a prespecified manner for the measurement operating state MBZ.

In step S6, a check is made to determine whether regeneration of the binary lambda probe is to be carried out. It may be necessary to carry out regeneration, for example, after a prespecified time period since the last time regeneration was carried out has elapsed and/or depending on probe contamination of the binary lambda probe 3 being identified and/or depending on a predefined distance being covered since the last time regeneration was carried out.

As an alternative or in addition, regeneration can also be carried out when, with desired rich operation of the internal combustion engine—possibly taking into account gas transit times—, the provided measurement signal of the binary lambda probe signals lean operation. As an alternative or in addition, regeneration can also be carried out when, with desired rich operation of the internal combustion engine—possibly taking into account gas transit times—, the potential difference between the first and the second electrode 5, 7 is negative.

If it is identified in step S6 that regeneration does not need to be carried out, the process is continued with step S5.

Otherwise, a check is made in step S7 to determine whether a prespecified condition is met and the internal combustion engine is in the overrun operation state in which the supply of fuel to the combustion chambers of the respective cylinders is suppressed and therefore air from the area surrounding the internal combustion engine, instead of exhaust gas, is located in the exhaust gas section.

The prespecified condition can be met, for example, after a prespecified further time period while the regeneration is carried out. If the prespecified condition is met and the overrun operation state is assumed in step S7, the process is continued with step S9 in which the current source is operated in the measurement operation state MBZ and, depending on the measurement signal MS of the binary lambda probe 3, an actuating signal STS is determined for the current source for the regeneration operation state of said current source, in order to set the prespecified oxygen concentration in the reference air volume 9.

In this connection, use is made of the knowledge that, during the overrun mode, the oxygen concentration of the gas mixture in the exhaust gas section corresponds substantially to that of the air surrounding the internal combustion engine. Therefore, in this way, the gas mixture in the exhaust gas section 1 in this case forms a reference for setting the prespecified oxygen concentration in the reference air volume 9 and can therefore be suitably used for determining the actuating signal STS for the current source in the regeneration operation state of said current source. In this connection, it is possible, for example, to determine a prespecified current intensity for the regeneration operation state and/or also duration of the application of the corresponding current intensity of the current by the current source 15 in the regeneration operation state RGBZ.

If the prespecified condition of step S7 is not met and possibly independently of whether the internal combustion engine is in its overrun operation state, the process is continued with step S11, in which, in order to set the prespecified oxygen concentration in the reference air volume 9, the current source 15 is operated in the regeneration operation state RGBZ, specifically for the purpose of setting the prespecified oxygen concentration in the reference air volume, wherein the actuating signal STS is set in accordance with the determined actuating signal in step S9. If step S9 has not yet been executed since the respective identification that regeneration is to be carried out, the actuating signal STS can initially have another prespecified value and/or profile. Following step S11, the process is again continued with step S3.

The process is again continued with step S3 at the latest after a prespecifiable residence time in the respective step S5, S9 or S11.

Regeneration can be terminated, for example, when it is established in step S9 that the prespecified oxygen concentration in the reference air volume 9 has been reached or has been approximately reached.

The current source and also the measurement signal transmitter can also be arranged independently of one another, in principle, outside the binary lambda probe, for example in the control device 19. However, they can also be designed individually or both in one physical unit with the binary lambda probe.

The measurement operation state MBZ differs from the regeneration operation state RGBZ, specifically, in particular, in that the current source is deactivated in the measurement operation state MBZ or activated in a different way than in the regeneration operation state RGBZ, while it is activated in the regeneration operation state RGBZ.

As an alternative, a voltage source can also be provided instead of the current source 15, said voltage source then having a resistor which is suitably electrically connected in series, in order to apply the respective current, depending on the operation state of the voltage source. Otherwise, operation of the voltage source is performed correspondingly analogously to the described procedure in respect of the current source.

What is claimed is:

1. A method for operating a binary lambda probe arranged in an exhaust gas section of an internal combustion engine and having a first electrode arranged on the exhaust gas side, a second electrode arranged outside of the exhaust gas side to adjoin a reference air volume fed air by a feed line communicating with an area outside of the internal combustion engine, an electrolyte in contact with both the first electrode on the exhaust gas side and with the second electrode, and a current source arranged electrically between the first and the second electrode, wherein a potential difference between the first and the second electrode forms a measurement signal of the binary lambda probe, the method comprising:
    communicating air from the area outside of the internal combustion engine into the reference volume,
    operating the current source in a measurement operation state during a measurement operation of the binary lambda probe, and providing the measurement signal,
    operating the current source in a regeneration operation state to set a prespecified oxygen concentration in the reference air volume, and
    when a prespecified condition is met and the internal combustion engine is in an overrun operation state in which a supply of fuel is suppressed:
        operating the current source in the measurement operation state, and
        determining an actuating signal for the current source for the regeneration operation state of said current source based on the measurement signal of the binary lambda probe to set the prespecified oxygen concentration in the reference air volume.

2. A method for operating a binary lambda probe arranged in an exhaust gas section of an internal combustion engine and having a first electrode arranged on the exhaust gas side, a second electrode arranged outside the exhaust gas side to adjoin a reference air volume fed air by a feed line communicating with an area outside of the internal combustion engine, an electrolyte in contact with the first electrode on the exhaust gas side and with the second electrode, and a current source arranged electrically between the first and the second electrode, wherein a potential difference between the first and the second electrode forms a measurement signal of the binary lambda probe, the method comprising:
    communicating air from the area outside of the internal combustion engine into the reference volume,
    operating the voltage source in a measurement operation state during a measurement operation of the binary lambda probe, and providing the measurement signal, operating the voltage source in a regeneration operation state to set a prespecified oxygen concentration in the reference air volume, and when a prespecified condition is met and the internal combustion engine is in an overrun operation state in which a supply of fuel is suppressed:

operating the voltage source in the measurement operation state, and determining an actuating signal for the voltage source for the regeneration operation state of said voltage source based on the measurement signal of the binary lambda probe in order to set the prespecified oxygen concentration in the reference air volume.

3. A device for operating a binary lambda probe arranged in an exhaust gas section of an internal combustion engine and having a first electrode arranged on the exhaust gas side, a second electrode arranged outside the exhaust gas side to adjoin a reference air volume fed air by a feed line communicating with an area outside of the internal combustion engine, an electrolyte in contact with the first electrode on the exhaust gas side and with the second electrode, and a current source arranged electrically between the first and the second electrode, wherein a potential difference between the first and the second electrode forms a measurement signal of the binary lambda probe, wherein the device is programmed:

to operate the current source in a measurement operation state during a measurement operation of the binary lambda probe, and providing the measurement signal, to operate the current source in a regeneration operation state to set a prespecified oxygen concentration in the reference air volume, and when a prespecified condition is met and the internal combustion engine is in an overrun operation state in which a supply of fuel is suppressed, after air from the area outside of the internal combustion engine enters into the reference volume:

to operate the current source in the measurement operation state, and to determine an actuating signal for the current source for the regeneration operation state of said current source based on the measurement signal of the binary lambda probe to set the prespecified oxygen concentration in the reference air volume.

4. A device for operating a binary lambda probe arranged in an exhaust gas section of an internal combustion engine and having a first electrode arranged on the exhaust gas side, a second electrode arranged outside the exhaust gas side to adjoin a reference air volume fed air by a feed line communicating with an area outside of the internal combustion engine, an electrolyte in contact with both the first electrode and the second electrode, and a voltage source arranged electrically between the first and the second electrode, wherein a potential difference between the first and the second electrode forms a measurement signal of the binary lambda probe, wherein the device is programmed:

to operate the voltage source in a measurement operation state during a measurement operation of the binary lambda probe, and providing the measurement signal, to operate the voltage source in a regeneration operation state to set a prespecified oxygen concentration in the reference air volume, and when a prespecified condition is met and the internal combustion engine is in an overrun operation state in which a supply of fuel is suppressed, after air from the area outside of the internal combustion engine enters into the reference volume:

to operate the voltage source in the measurement operation state, and to determine an actuating signal for the voltage source for the regeneration operation state of said voltage source based on the measurement signal of the binary lambda probe in order to set the prespecified oxygen concentration in the reference air volume.

* * * * *